United States Patent [19]

King

[11] Patent Number: 5,848,587
[45] Date of Patent: Dec. 15, 1998

[54] AEROSOL MEDICATION DELIVERY SYSTEM

[75] Inventor: Russell W. King, Baldwin Park, Calif.

[73] Assignee: Medi-Nuclear Corporation, Inc., Baldwin Park, Calif.

[21] Appl. No.: 826,554

[22] Filed: Apr. 4, 1997

Related U.S. Application Data

[63] Continuation-in-part of Ser. No. 531,697, Sep. 21, 1995, Pat. No. 5,617,844.

[51] Int. Cl.$^6$ .................................................. A61M 11/00
[52] U.S. Cl. ............................... 128/200.18; 128/200.14; 128/200.23
[58] Field of Search .......................... 128/200.14, 200.18, 128/200.23

[56] References Cited

U.S. PATENT DOCUMENTS 3,187,748  6/1965  Mitchell et al. .................... 128/200.23
5,617,844  4/1997  King .................................. 128/200.18

Primary Examiner—Aaron J. Lewis
Attorney, Agent, or Firm—James E. Brunton

[57] ABSTRACT

An aerosol medication delivery apparatus which includes a novel particle generator for generating very small particles of medicament, a valving mechanism and an expansion chamber which permits medication to be delivered to the patient through a conventional inhalation mouthpiece or face mask. The apparatus also includes a filter unit for filtering the patient's exhaled breath and a unique baffling arrangement which functions to decrease average aerosol particle size for better targeting of the desired lung area. In one form of the invention, the particle or aerosol generator operates on a direct pressure technique wherein an elastomeric delivery tube is intermittently compressed and released to generate the very small particles of medicament.

12 Claims, 5 Drawing Sheets

AEROSOL MEDICATION DELIVERY SYSTEM

This is a Continuation-In-Part of application Ser. No. 08/531,697 filed Sep. 21, 1995, now U.S. Pat. No. 5,617,844.

BACKGROUND OF THE INVENTION

1. Field of the Invention

The present invention relates to aerosol medication delivery systems. More particularly, the invention concerns an improved aerosol inhalation apparatus that is very useful for dispensing pharmaceuticals in the treatment of respiratory or pulmonary diseases and for systemic delivery of drugs via aerosolization.

2. Discussion of the Prior Art

Therapeutic aerosols are commonly administered to patients suffering from numerous types of pulmonary diseases. Specific medications, include $beta_2$ agonists, anticholinergies, cromolyn sodium, and steroids. More recently the aerosol method of delivery has been used to administer Pentamidine to patients afflicted with AIDS, and is presently under consideration as a delivery means for insulin in the treatment for diabetes. Experience has shown that the use of aerosols to treat lung disease is highly advantageous in that it produces optimal therapy with minimum side effects. Both physical and clinical factors affect aerosol deposition in the lungs. Physical factors include inertial impaction, sedimentation, and diffusion. Clinical factors include particle size, ventilatory pattern and lung function. Aerosols larger than 5 micron aerodynamic diameter (AD) poorly penetrate the upper respiratory tract. Those in the 0.2 to 2 micron range tend to have their maximum disposition in the lung parenchyma.

In general the devices used for producing medical aerosols fall into three categories; the small volume nebulizer (SVN), the metered does inhaler (MDI), and the powder dose inhaler (PDI).

Although the small volume nebulizer (SVN) has traditionally been the apparatus of choice for delivery of therapeutic aerosols, many institutions are now switching to the MDI. The small volume nebulizer (SVN) apparatus typically consists of disposable or reusable nebulizer, a mouthpiece or face mask, and a pressurized gas source usually oxygen or air. The metered dose inhaler (MDI), on the other hand, typically contains the active drug, a metering valve, and chlorofluorocarbon (CFC) propellants. The drug containing canister of the device is generally fitted to a mouthpiece actuator, and activation by compression of the canister into the mouthpiece results in the release of a unit dose of medication.

There is extensive literature indicating the successes of aerosol therapies, as well as the difficulties of using the aerosols properly. See, for example, Respiratory Infection: Diagnosis and Management. J. E. Pennington ed. Raven Press, N.Y. chest 1981, 80:911–915: Arch, Int. Med. 1973, 131:88–91. Notwithstanding the very considerable development of aerosols and methods of using the same, there is still room for improvement in the administration of pharmaceutical aerosols.

A major problem of aerosol therapy is to deposit the aerosol on the walls of small bronchi and bronchioles, where the action of the medication is most often required. Less than 10% of the medication delivered by standard multidose inhalers reaches the typical patient's lungs. Most of the 90% of the medication which does not penetrate the target area is deposited in the mouth, throat, and trachea, and is eventually injested. A small fraction of the aerosol is exhaled.

For effective utilization, the aerosol should consist of small particles, less than 5 microns AD, since larger particles cannot negotiate the sharp turns to the lung and are deposited in the orophapyny due to inertial effects. In order to minimize mouth deposition further it has been shown that the volumetric flow rate of the inhaled aerosol should be below 30 liters per minute. Meter dose inhalers deliver aerosol at a high initial velocity directly into the patient's mouth. This high initial velocity of the aerosol is a major factor in the ineffectiveness of many inhaler systems.

Another serious problem inherent in MDI aerosol medication is patient timing coordination. If patient inhalation does not occur on a timely basis with MDI canister actuation, a large percentage of the medication is lost.

Several pharmaceutical manufacturers have included, or sold separately with their MDI aerosol products, what are referred to variously as "spacers", "oral adaptors", "space-inhalers", and "spray inhalers" to be used in conjunction with their products. These offer only a partial solution to the problems which typically occur in MDI aerosol delivery.

The apparatus of the present invention provides a very substantial improvement over all prior art MDI-type devices in that it addresses: (1) volumetric flow rate of medication, (2) elimination of patient coordination problems, (3) particle size, and (4) environmental protection considerations.

A somewhat similar aerosol medication delivery system is disclosed in co-pending application Ser. No. 08/531,697 filed by the present inventor. Accordingly, this application, Ser. No. 08/531,697, is hereby incorporated herein by reference as though fully set forth herein. Reference to this earlier-filed application will show that the device of the present invention embodies a drug nebulizing means of a generally different construction and mode of operation than that disclosed in Ser. No. 08/531,697.

SUMMARY OF THE INVENTION

It is an object of the present invention to provide an inhalation apparatus, which, when used with an MDI-type inhaler, will result in a substantial increase in the delivery to the patient of particles in the respirable size range.

Another object of the invention is to provide an apparatus of the aforementioned character which essentially eliminates patient timing coordination problems when administering a unit does of medication.

Another object of the invention is to provide an apparatus which limits volumetric flow rate of the inhaled aerosol to that of normal patient breathing, i.e. below 30 liters per minute.

Another object of the invention is to provide a novel apparatus wherein release of medication from the MDI canister is triggered automatically by patient exhalation rather than by manual actuation, thereby providing for timely accessibility during the next inhalation.

Yet another object of the invention is to provide an apparatus of the character described wherein the number of desired patient inhalations can be preselected, and wherein medication availability will automatically terminate upon reaching that number.

Another object of the invention is to provide an apparatus of the character described in the preceding paragraphs which embodies a novel aerosol particle generator which operates on a direct pressure technique wherein an elastomeric delivery tube is intermittently compressed and released to generate very small particles of medicament.

Still another object of the invention is to provide an apparatus as described in the preceding paragraphs wherein air exhaled from the patient is safely filtered before it is released to room atmosphere.

DESCRIPTION OF THE INVENTION

Figure 1:
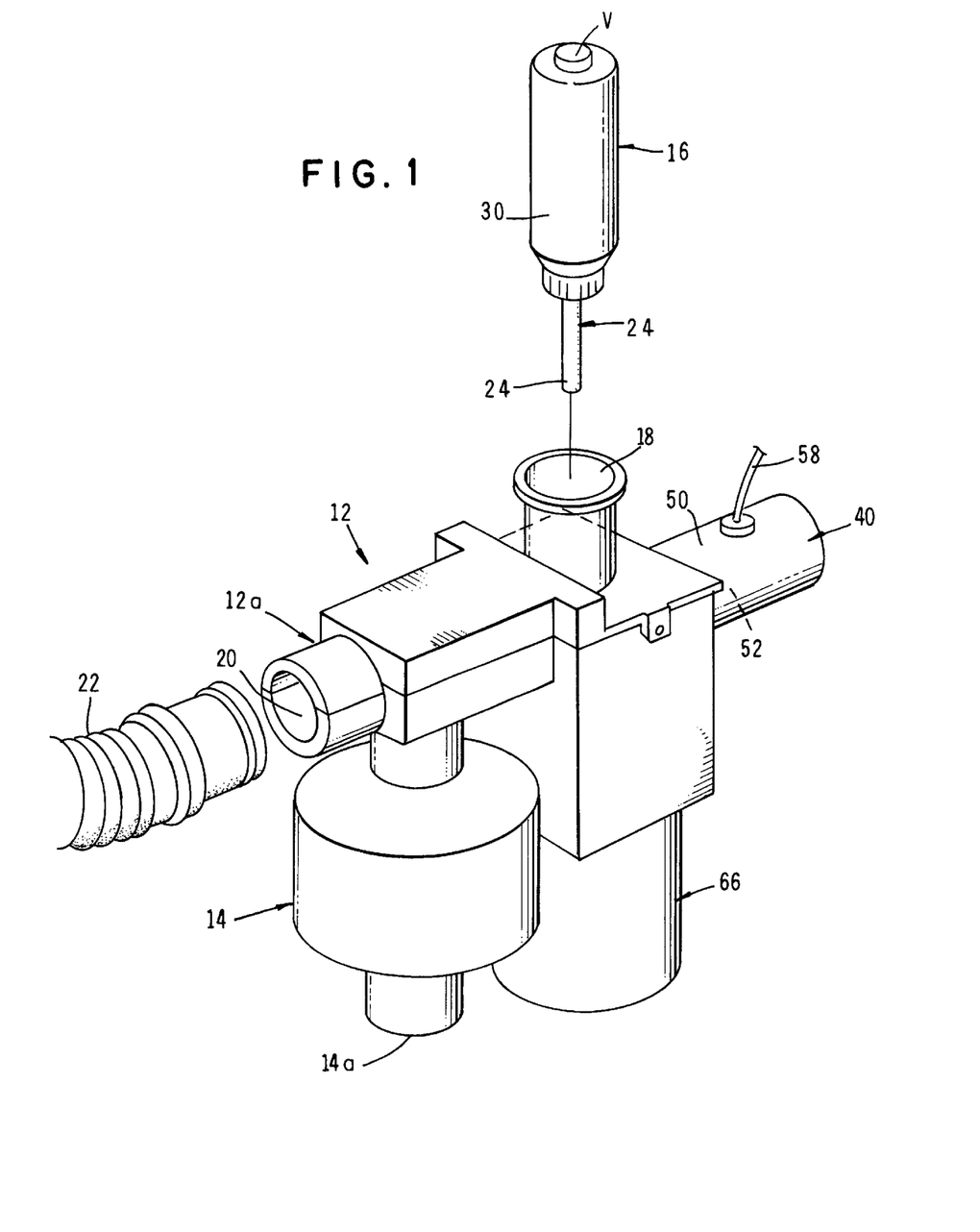
FIG. 1 is a generally perspective, exploded view of one form of the aerosol medication delivery system of the invention.
Figures 2, 10, 11:
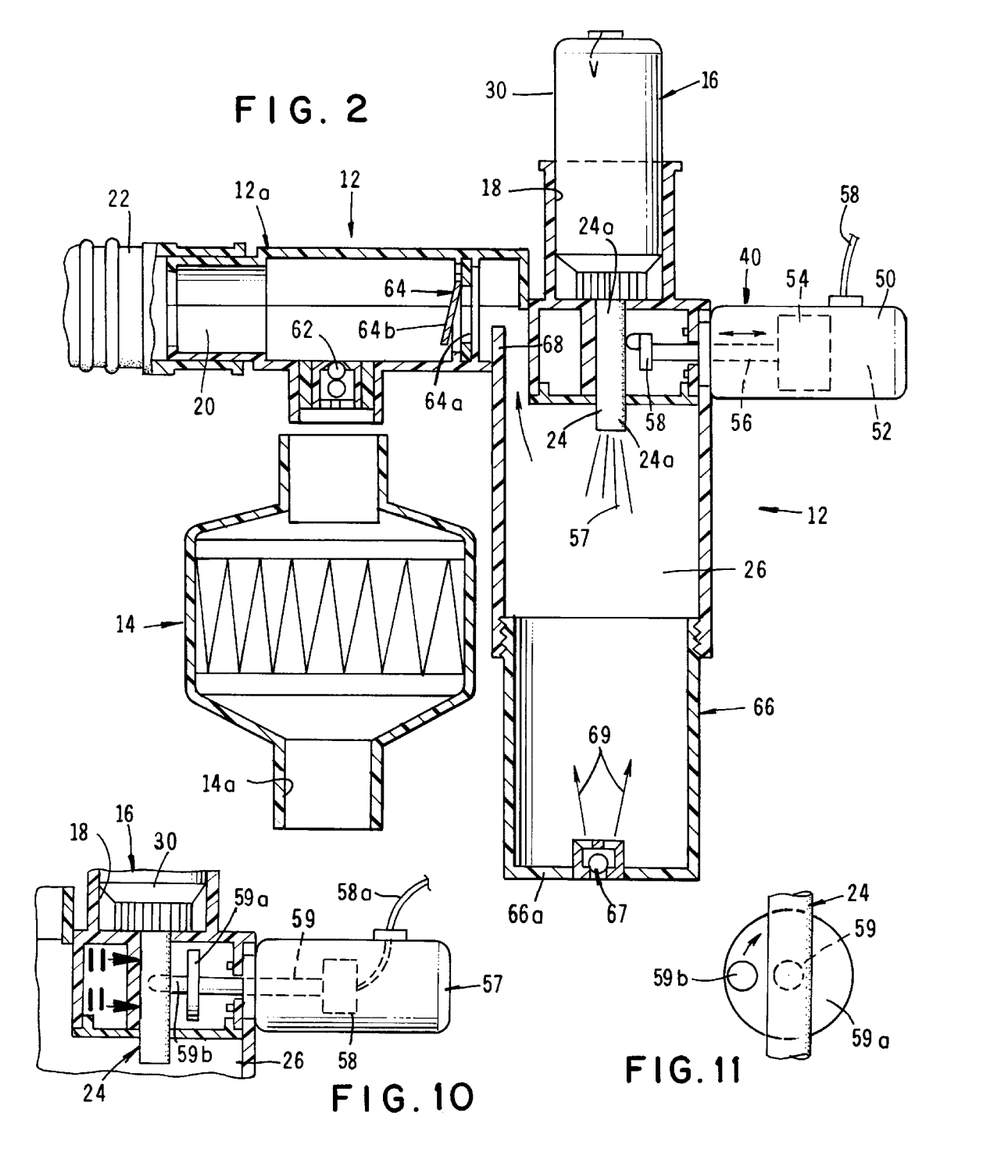
FIG. 2 is a side-elevational, cross-sectional view of the assembled apparatus shown in FIG. 1.
FIG. 10 is a fragmentary, cross-sectional view of an alternate form of flow activator means of the invention.
FIG. 11 is a view taken along lines 11—11 of FIG. 10.
Figure 3:
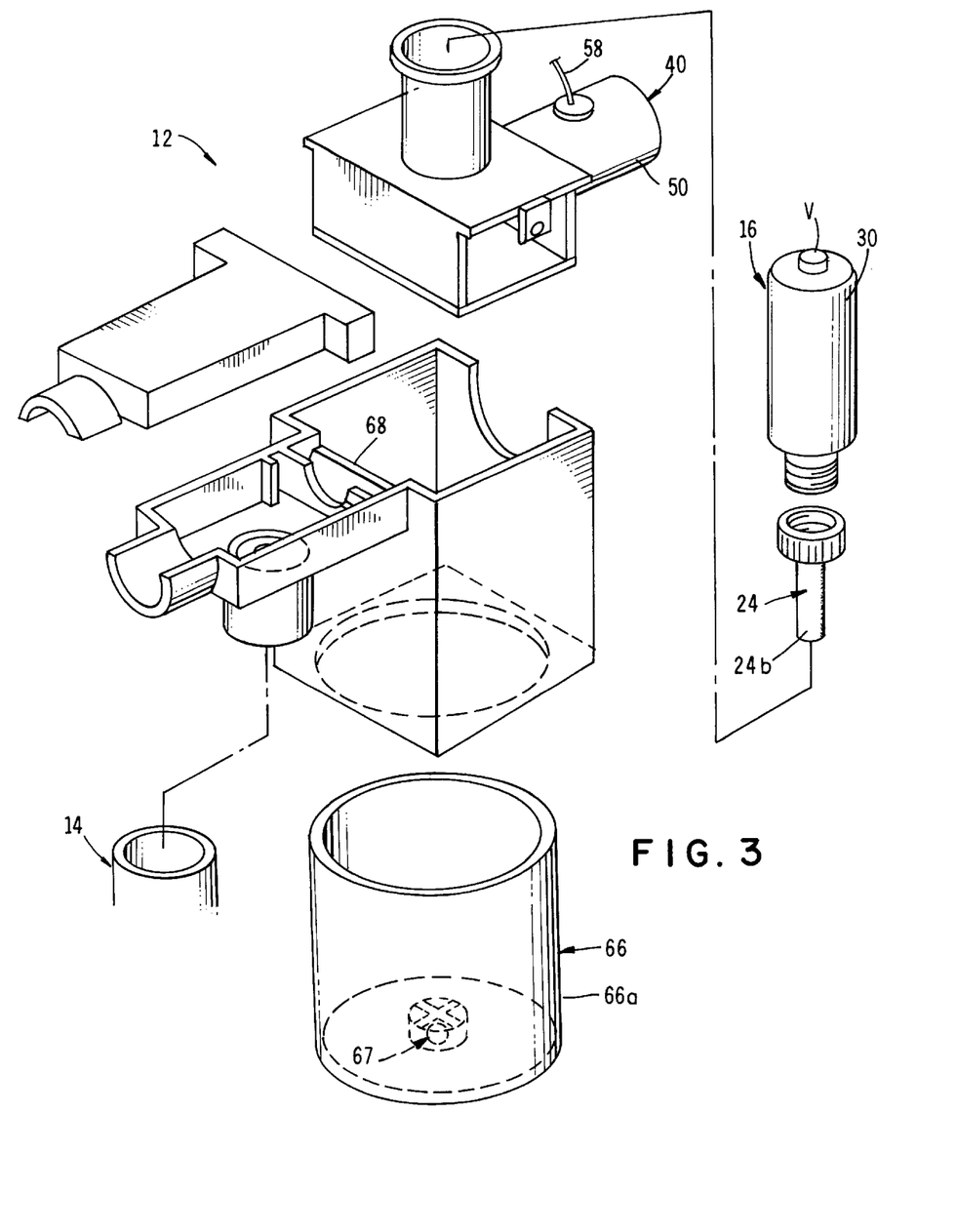
FIG. 3 is an enlarged, generally perspective, further exploded view of the form of apparatus shown in FIGS. 1 and 2.

Referring to the drawings and particularly to FIGS. 1, 2, and 3, the aerosol inhalation apparatus of one form of the present invention can be seen to comprise a sectionalized main housing 12 to which is attached filtering means, here provided as a bacteria filter assembly 14 and a drug nebulizing means, shown here as a novel aerosol particle generator 16 for generating aerosol particles by a direct pressure technique. As best seen in FIGS. 1 and 2, generator 16 is removably mounted within an easily accessible chamber 18 which forms a part of housing 12.

Provided proximate the first end 12a of housing 12 is inhalation means comprising a standard size breathing port 20 which is coupled with the patient via a flexible conduit 22 and an appropriate mouthpiece, or face mask (not shown). In a manner presently to be described, the various components and interconnecting fluid flow passageways of the device are uniquely constructed and arranged to maximize the delivery of properly sized aerosolized medication to the patient on a timely basis.

Figures 4, 5, 6, 7:
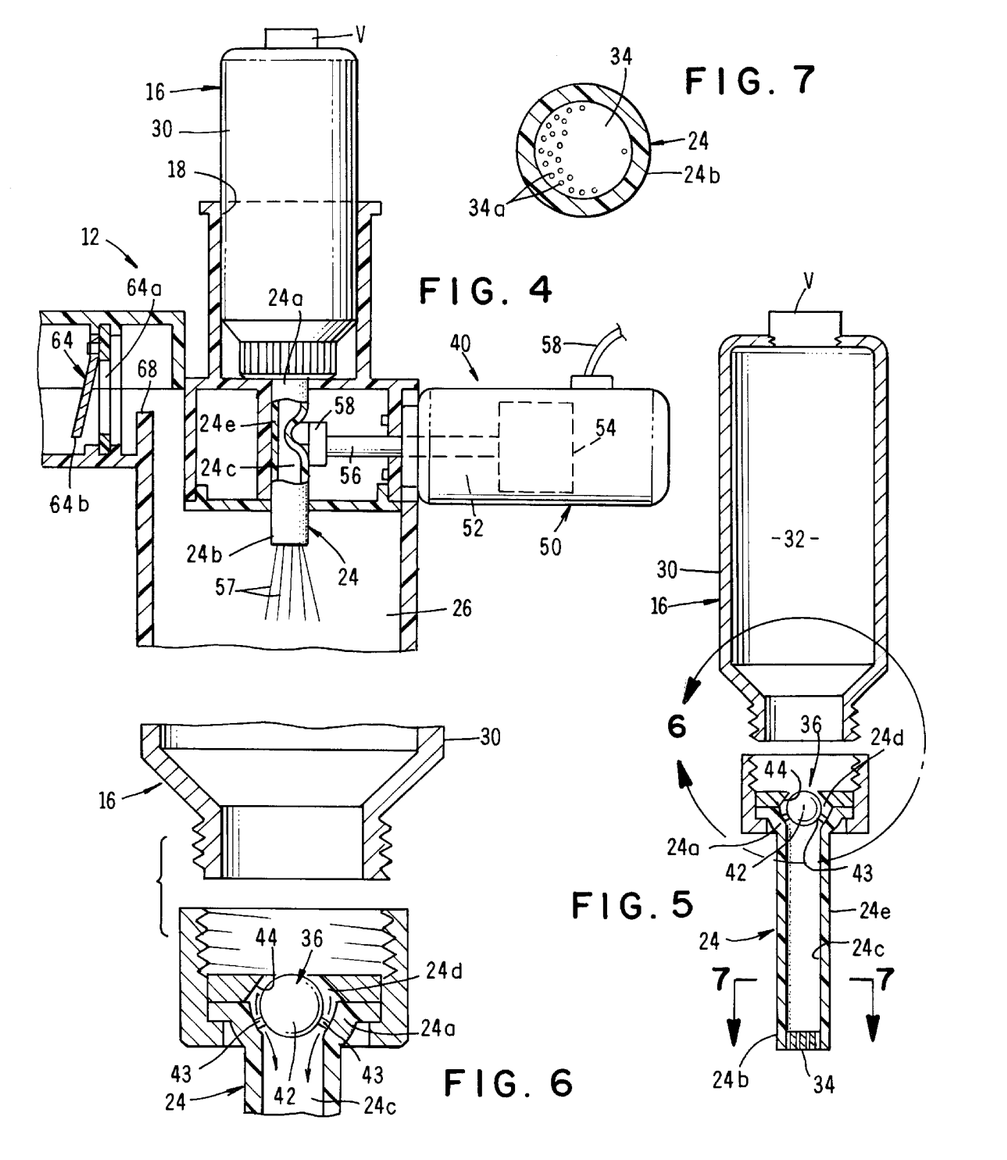
FIG. 4 is a fragmentary, cross-sectional view of the right-hand portion of the apparatus shown in FIG. 2.
FIG. 5 is a side-elevational view of the mist generator portion of the apparatus partly in cross section to show internal construction.
FIG. 6 is an enlarged, cross-sectional view of the area designated as 6 in FIG. 5.
FIG. 7 is a cross-sectional view taken along lines 7—7 of FIG. 5.

Turning particularly to FIGS. 2 and 5, it can be seen that the nebulizing means, or generator 16 of the apparatus is mounted within chamber 18 in a manner such that the outlet tube 24 of the device extends downwardly into an expansion chamber 26 formed in housing 12. Outlet tube 24, which is constructed from a resiliently compressible, elastomeric material such as polyethylene, is connected proximate its first end 24a with a container 30 having a drug containing reservoir 32. Provided proximate and partially closing the second end 24b of outlet tube 24 is a closure means shown here as a perforated wafer 34 (FIG. 7).

Disposed between wafer 34 and reservoir 32 is a valve means, which is here provided in the form of a normally open check valve assembly 36 which functions to control the flow of the fluid contained within reservoir 32 outwardly of the reservoir and into the internal passageway 24c of tube 24.

By way of background, the controlled generation of aerosol particles by nebulizers of the character described in Ser. No. 08/531,697 is, of course, well known. However, aerosol particles can also be generated when sufficient pressure is applied to a liquid to force it through small apertures at a velocity sufficient to form very small fluid jets. These small fluid jets will effectively break up under the influence of surface tension effects to form an aerosol comprising a multiplicity of very small particles. This direct pressure technique has been used for more than twenty years in creating fog (aerosol droplets in the 10–20 micron range) for cooling and for various agricultural purposes. More recently, the technique has been used for producing medical aerosols. (See, for example, "*A New Unit Dose, Breath Actuated Aerosol Drug Delivery System*", Peter Lloyd et al, Respiratory Drug Delivery V, Apr. 28, 1996–May 2, 1996 Phoenix, Ariz.)

In the particle generator of the apparatus of the present invention, high pressure surges are applied to the liquid medicament contained within the delivery tube of the device in a manner to produce aerosol particles from aliquots of liquid medicament contained within an internal passageway 24c of the tube 24 thereby producing a continuous supply of aerosol medication for patient use. This novel generator, when integrated into the delivery system of the apparatus will, in a manner presently to be described, efficiently provide continuous nebulization without, in any way, sacrificing the compactness, simplicity and portability of the apparatus.

As shown in FIG. 7, perforated wafer 34 is provided with a multiplicity of small apertures 34a which are preferably on the order of 2 microns in size. With this construction, when the liquid medicament contained within passageway 26c of the tube is forced through wafer 34 at a very high velocity, a fine particulate laden spray will be produced. Wafer 34 can be constructed of a porous ceramic, a sinteed metal, or a thin metal or ceramic disc which has been precisely laser drilled. The spray produced by this pressure technique comprises a multiplicity of medicament particles of various sizes which are expelled under pressure into expansion chamber 26 that is disposed immediately below chamber 18 and into which end 24a of tube 24 extends.

To exert pressure on the aliquot of fluid contained within the delivery tube so as to cause the medicament particles to be controllably expelled into expansion chamber 26, a novel flow actuator means is provided. In one embodiment of the invention, the actuator means comprises an actuator assembly 40 which includes compression means for intermittently compressing and releasing the side wall 24e of tube 24 with sufficient force to cause the production of the particulate laden spray in the manner shown in FIG. 4. This compression of the side wall of the tube by the compression means changes the internal, cross-sectional configuration of the tube from being generally circular to being generally elliptical, thereby sharply reducing the volume of the internal passageway of the tube.

As previously mentioned, valve means are provided to control the flow of fluid from reservoir 32 into tube 24. These valve means, which comprise valve assembly 36, includes a generally spherical valve member 42 which is disposed within an enlarged neck portion 24d of tube 24. Member 42 is movable from the first valve open position shown in FIGS. 5, 6 and 8, where it is supported within neck portion 24d by circumferentially spaced legs 43, to a valve closed position shown in FIG. 9 where it seats against an internal valve seat 44 provided proximate neck 30a of container 30. In a manner presently to be described, valve member 42 moves into the second valve closed position in response to fluid pressure generated within the internal passageway 24c of the tube 24 by the flow actuator means of the invention. When valve member 42 is in the valve open position shown in FIG. 8, the liquid medicament contained within reservoir 32 is free to flow by force of gravity into and substantially fill the internal passageway 24c of tube 24. To permit proper venting during the tube-fill step, vent means "V" in the form of a small screw cap (FIG. 5) is provided.

In one form of the invention, the important flow actuator means comprises a tube compression means or compression assembly 40 which is connected to housing 12 in the manner shown in FIG. 2. Assembly 40 includes a body 50 having a chamber 52 within which a piston 54 is reciprocally carried. Connected to piston 54 and extended outwardly from body 50 is an actuator shaft 56 which has a tube compressing protuberance 58 formed proximate the end thereof. When piston 54 and shaft 56 are moved outwardly from the first position shown in FIG. 8 to the tube compression position shown in FIG. 9, substantial pressure will be exerted on the fluid within tube 24 causing valve member 42 to rapidly move into the valve closed position shown in FIG. 9. This sharp exertion of pressure on the fluid trapped within the now closed passageway 24c of tube 24 will force the fluid through the apertures 34a formed in wafer 34 with sufficient force to form a multiplicity of very fine fluid jets 57 (FIG. 4). These jets, under the influence of surface tension effects will break up into aerosol droplets of various sizes as, for example, droplets in the 10 to 20 micron size range. Repeated rapid intermittent compression and relaxation of tube wall 24e by the flow actuator means will produce a consistent, uniform flow of very small aerosol particles into expansion chamber 26 in the manner shown in FIG. 4.

Piston 54 can be reciprocated within chamber 52 of body 50 by hydraulic or pneumatic means in a manner well known to those skilled in the art. When piston 54 is driven hydraulically or pneumatically, the driving fluid can be introduced into chamber 52 via conduit 58 (FIG. 4). Piston 54 can also be reciprocated within chamber 52 electrically using a solenoid arrangement of a character well known to those skilled in the art.

Additional forces can be exerted on tube wall 24e by other mechanical means such as those shown in FIGS. 10 and 11 of the drawings. In the alternate form of flow actuator of the invention shown in these figures, the tube compression means or compressor assembly, comprises a body 57 which houses motor means provided as an electric motor 58 which controllably rotates a shaft 59. Provided at the end of shaft 59 is wheel 59a upon which a tube engaging protuberance 59b is eccentrically mounted. Motor 58 is energized via an electrical conduit 58a and, when energized, causes shaft 59 to rotate in a manner to bring protuberance 59b into pressural contact with tube 24 twice for each resolution of the shaft. As the protuberance compresses, the tube fluid contained within passageway 24c will be forced outwardly through wafer 34 to form the particulate laden spray.

Figure 8:
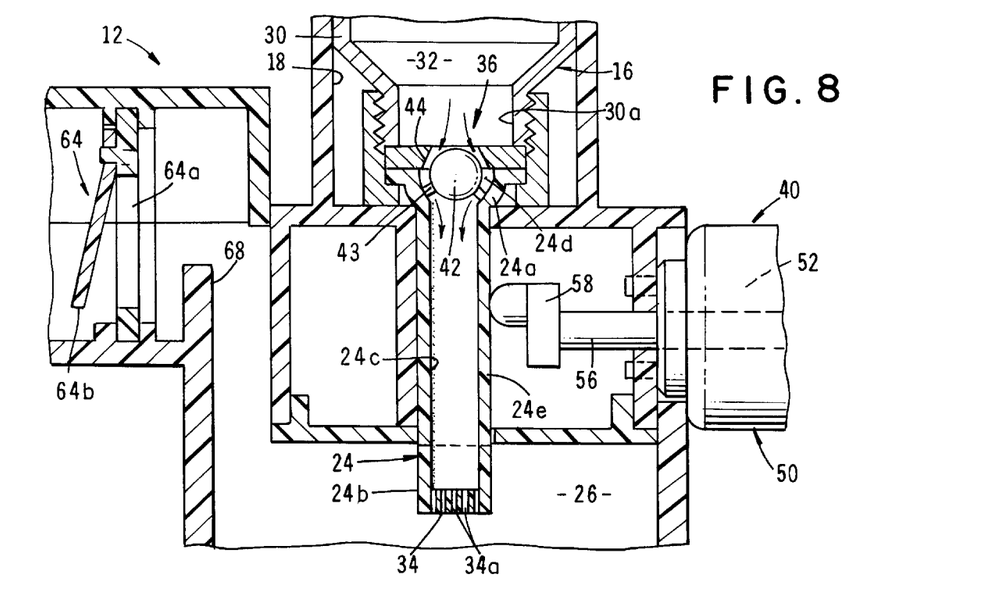
FIG. 8 is a greatly enlarged cross-sectional view of the lower portion of the mist generator portion of the apparatus illustrating the construction of the check valve assembly thereof and further showing the mechanism for activating spray generation.

Without regard to the particular mechanism used to intermittently compress tube wall 24e when pressure on the wall is intermittently released, the valve member will move into the open position shown in FIG. 8 thereby permitting another aliquot of medicament to flow from reservoir 32 into tube 24. In the manner previously described, this novel and efficient pressure technique will simply and reliably provide a continuous controlled flow of very small particles of medicament into expansion chamber 26.

Obviously, the amount of drug medication being converted to aerosol is determined by the volume of liquid displaced per actuation of the actuator means and the number of actuations per minute. The rate of compression and relaxation of tube wall 24e can readily be controlled to provide a precise aerosol generation rate. Therefore, it is readily apparent that novel pressure technique of the invention as described in the preceding paragraphs can be optimized for drug delivery to meet a wide variety of clinical demands.

During use of the apparatus in patient treatment, the patient's exhaled air is received by filter assembly 14 via a first valve means, shown here as a one-way ball check valve 62 of standard construction. During patient exhalation, a nominal amount of resistance to air flow is caused by valve 62 which creates a slight over pressure in a second forward chamber 20, thereby maintaining the novel flow control or pivoting valve assembly 64 of the invention in a closed position. Accordingly, if the particle generator means is actuated during patient exhalation, the aerosolized medicament produced thereby is securely contained with expansion chamber 26 for use during the next patient inhalation.

Upon patient inhalation, valve assembly 64 opens so that all medication from chamber 26 is carried through chamber 20 and into the patient's lungs via conduit 22 and the mouthpiece or face mask. If the particle generator means is actuated during the time of patient inhalation, the medication will, of course, enter the air stream and flow directly to the patient's lungs. Thus, the system as described uniquely provides for delivery of the desired patient dose with no concern as to the timing of medication released from the particle generator device. Also, the flow rate of medication to the patient is strictly a function of patient breathing only, thereby optimally allowing the medication to clear the patient's throat area and flow freely into the patient's lower lung compartments.

Figure 9:
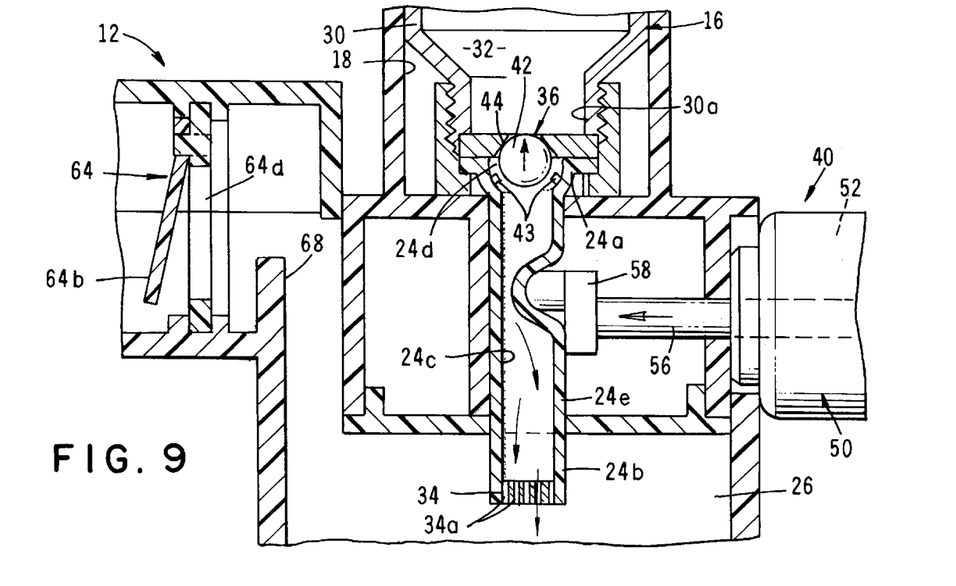
FIG. 9 is a cross-sectional view similar to FIG. 8, but showing the components of the device moved into a valve-closed, mist-activating configuration.

As indicated in FIGS. 8 and 9, the flow control means, or assembly 64, is of substantially identical construction and operation to the flow control means 40 described in Ser. No. 08/531,697 which is incorporated herein by reference. Accordingly, this important flow control means will not be further discussed in detail herein.

Connected to chamber 26 and in communication therewith is settling means shown here as a settling chamber 66 which is threadably connected to housing 12 and functions to remove large particles from the particulate laden mist by means of sedimentation. The provision of a baffle means, here comprising an upstanding wall 68 (FIGS. 2 and 4) which interferes with the flow of the larger particles, also contributes to the reduction of the number of large particles contained within the particulate laden spray which reach the patient.

As is the case with the form of the invention described in Ser. No. 08/531,697, the apparatus of the present invention will function equally well with or without filter assembly 14. In those instances where medicament should not be released to the environment, a filter means such as filter assembly 14, which is identical to that described in the application incorporated herein by reference, can be provided to filter particles from the spray flowing into chamber 20 and outwardly to atmosphere via outlet port 14a as a result of patient exhalation.

In operating the apparatus of the present form of the invention, the particle generator 16 is first inserted into chamber 18 in the inverted position shown in FIG. 2 so that end 24b of tube 24 is received within expansion chamber 26. With the generator thusly positioned, the liquid medicament contained within the generator will flow into tube 24 via normally open valve assembly 36. Operation of the flow actuator means will then cause a medicament laden mist to plume outwardly from end 24a of tube 24 and into expansion chamber 26 in the manner shown in FIG. 4.

Upon patient inhalation, a conventional check valve assembly 67 which is mounted within the base 66a of a housing 66 that is threadably connected to housing 12 will open permitting air to enter expansion chamber 26 in the direction of the arrows identified by the numerals 69 in FIG. 2. This air will mix with the particulate laden mist and will flow upwardly of the device through passageway 64a where it will impinge upon diaphragm 64b of valve assembly 64 causing it to pivot into the open position shown in FIG. 4. As the mixture of air and particulate laden mist enters chamber 20, valve 62 will be urged into its closed position and the particulate laden mist and air mixture will enter flexible conduit 22 and flow toward the patient.

As in the earlier described embodiments, the baffle means or baffle wall 68 partially blocks entrance to chamber 20 and impedes the progression of the larger particles contained within the particulate laden mist as the mist tends to flow toward chamber 20. Baffle wall 68 is strategically located and designed so that the larger particles, contained within the particulate laden mist, will be unable to pass over the barrier and will fall by force of gravity into chamber 26. This important aspect of the invention prevents the undesirable flow of larger particles of medicament toward the patient via chamber 20.

When the patient exhales, check valve 62 will move into the open position permitting the exhaled breath to enter filter assembly 14 were it is completely filtered prior to entering the atmosphere via outlet port 14a of the device. With this unique construction, upon patient exhalation, the flexible diaphragm member 64b of flow control means or assembly 64 will close, blocking fluid flow through opening 64a.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid delivery apparatus comprising:
   (a) a housing having interconnecting first and second chambers;
   (b) flow control means carried by said housing for controlling passage of fluid between said first and second chambers;
   (c) particle generator means connected to said housing for introducing a fluid into said first chamber of said housing, said particle generator means comprising:
      (i) container having a fluid reservoir;
      (ii) an elongated tube connected to said container, said tube having a side wall defining a fluid passageway and having first end connected to said container, said tube being constructed of a resiliently compressible, elastomeric material and having a second end extending into said first chamber;
      (iii) a closure means connected to said second end of said tube for partially closing said second end, said closure means comprising a wafer having a multiplicity of small apertures therethrough;
      (iv) flow actuator means for exerting intermittent forces of said side wall of said tube; and
      (v) valve means for controlling fluid flow between said reservoir of said container and said fluid passageway of said tube, said means comprising a normally open valve movable from first open position to a second closed position as a result of forces being exerted on said side wall of said tube by said flow actuator means.

2. An apparatus as defined in claim 1, in which said housing further includes a wall having an opening therein, said wall being disposed intermediate said first and second chambers and in which said flow control means comprises a valve member pivotally movable relative to said opening in said wall.

3. An apparatus as defined in claim 1 in which said housing includes an outlet port in communication with atmosphere, and in which said apparatus further includes filtering means connected to said housing for filtering particulates from the particulate-laden mist flowing through said outlet port.

4. An apparatus as defined in claim 1 in which said flow actuator means comprises tube compression means for alternatively compressing and releasing said side wall of said tube.

5. An apparatus as defined in claim 4 in which said tube compression means comprises a compression assembly including:
   (a) a body having a chamber;
   (b) a shaft extending outwardly from said body; and
   (c) a tube engaging protuberance connected to said shaft for intermittently, pressurally engaging said tube.

6. An aerosol inhalation apparatus for delivering a medicament containing mist to a patient comprising:
   (a) a housing having interconnecting first and second chambers and including a wall having an opening therein, said wall being disposed between said first and second chambers;
   (b) flow control means carried by said housing for controlling passage of fluid between said first and second chambers, said flow control means comprising a valve means for opening and closing said opening in said wall;
   (c) particle generator means connected to said housing for introducing a fluid into said first chamber of said housing, said particle generator means comprising:
      (i) a container having a fluid reservoir;
      (ii) an elongated tube connected to said container, said tube having a side wall defining a fluid passageway and having first end connected to said container, said tube being constructed of a resiliently compressible, elastomeric material and having a second end extending into said first chamber;
      (iii) a closure means connected to said second end of said tube for partially closing said second end, said closure means comprising a wafer having a multiplicity of small apertures therethrough;
      (iv) valve means for controlling fluid flow between said reservoir of said container and said fluid passageway of said tube, said means comprising a normally open valve movable from first open position to a second closed position; and (v) flow actuator means for exerting intermittent forces of said side wall of said tube, said flow actuator means comprising tube compression means for alternately compressing and releasing said side wall of said tube.

7. An apparatus as defined in claim 6 in which said tube compression means comprises a compression assembly including:

(a) a body having a chamber;

(b) a shaft extending outwardly from said body; and (c) a tube engaging protuberance connected to said shaft for intermittently pressurally engaging said tube.

8. An apparatus as defined in claim 7 in which said compression assembly further includes a piston reciprocally movable within said chamber, said shaft being connected to said piston.

9. An apparatus as defined in claim 7 in which said compression assembly further includes a motor means carried within said chamber for rotating said shaft to move said tube engaging protuberance intermittently into engagement with said tube.

10. An aerosol inhalation apparatus for delivering a medicament containing mist to a patient comprising:

(a) a housing having interconnecting first and second chambers and including a wall having an opening therein, said wall being disposed between said first and second chambers;

(b) flow control means carried by said housing for controlling passage of fluid between said first and second chambers, said flow control means comprising valve means for opening and closing said opening in said wall, said valve means comprising a valve member pivotally connected to said housing proximate said opening in said wall;

(c) particle generator means connected to said housing for introducing a fluid into said first chamber of said housing, said particle generator means comprising:

(i) container having a fluid reservoir;

(ii) an elongated tube connected to said container, said tube having a side wall defining a fluid passageway and having first end connected to said container, said tube being constructed of a resiliently compressible, elastomeric material and having a second end extending into said first chamber;

(iii) a closure means connected to said second end of said tube for partially closing said second end, said closure means comprising a wafer having a multiplicity of small apertures therethrough;

(iv) valve means for controlling fluid flow between said reservoir of said container and said fluid passageway of said tube, said means comprising a normally open valve movable from first open position to a second closed position; and (v) flow actuator means for exerting in termittent forces of said side wall of said tube, said flow actuator means comprising tube compression means for alternately compressing and releasing said side wall of said tube, said tube compression means comprising a compression assembly including:

a. a body having a chamber;

b. a shaft extending outwardly from said body; and c. a tube engaging protuberance connected to said shaft for intermittently, pressurally engaging said tube.

11. An apparatus as defined in claim 10 in which said compression assembly further includes a piston reciprocally movable within said chamber, said shaft being connected to said piston.

12. An apparatus as defined in claim 11 in which said compression assembly further includes a motor means carried within said chamber for rotating said shaft to move said tube engaging protuberance intermittently into engagement with said tube.

* * * * *